United States Patent
Belkin

Patent Number: 6,110,136
Date of Patent: Aug. 29, 2000

[54] DIGIT SPLINT DEVICE AND METHOD OF USE

[76] Inventor: Julie Belkin, 1610 Pincay Ct., Annapolis, Md. 21401

[21] Appl. No.: 09/175,741

[22] Filed: Oct. 20, 1998

Related U.S. Application Data

[60] Provisional application No. 60/064,968, Nov. 8, 1997.

[51] Int. Cl.[7] .................................. A61F 5/00; A61F 5/37
[52] U.S. Cl. ............................................ 602/22; 128/880
[58] Field of Search ........................ 602/5–7, 20–22; 128/878–880

[56] References Cited

U.S. PATENT DOCUMENTS

| | | | |
|---|---|---|---|
| 3,170,460 | 2/1965 | Stilson | 602/22 |
| 4,243,026 | 1/1981 | Barber | 602/22 |
| 4,270,528 | 6/1981 | Hanson | 602/22 |
| 4,297,992 | 11/1981 | LaRue et al. | 602/22 |
| 4,441,489 | 4/1984 | Evans et al. | 602/22 |
| 4,674,487 | 6/1987 | Schaeffer | 602/22 |
| 4,770,166 | 9/1988 | Garris | 602/22 |
| 4,932,396 | 6/1990 | Garris | 602/22 |
| 5,520,626 | 5/1996 | Schaeffer | 602/22 |

*Primary Examiner*—Stephen R. Crow
*Assistant Examiner*—Denise Pothier
*Attorney, Agent, or Firm*—Plunkett & Cooney, P.C.

[57] ABSTRACT

A digit splint is defined by an arcuate angularly inclined base and an ovoid which extends upwardly and radially outward from the base. The base is positioned on the palmar side of a joint of a digit and the ovoid conforms to the dorsum of a digit when the digit is in an extended position without hyperextension. The ovoid has two substantially parallel sides which, when worn, conform to impinge on the sides of the joint of a digit at the axis to provide lateral stability at the joint of a digit and to prevent migration of the splint on a digit. The splint also prevents hyperextension of the joint of a digit. In an alternate configuration, the splint may be rotated 180 degrees about the horizontal axis on a joint of a finger. In this configuration, the splint provides lateral stability at a joint of a digit and corrects flexion at a joint of a digit.

2 Claims, 3 Drawing Sheets

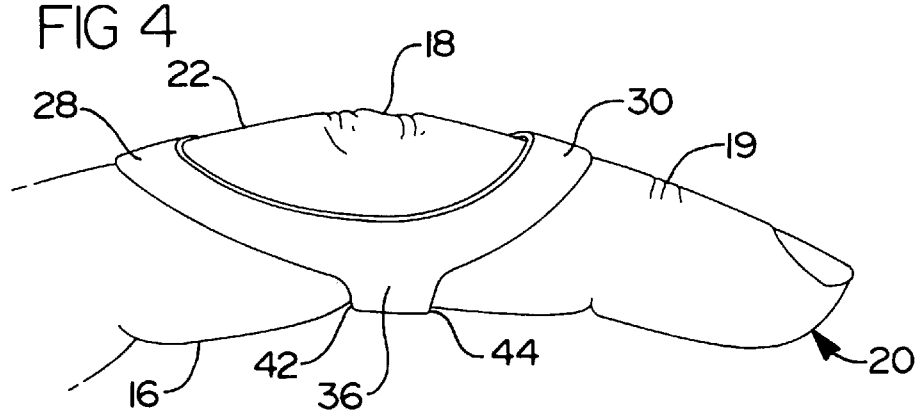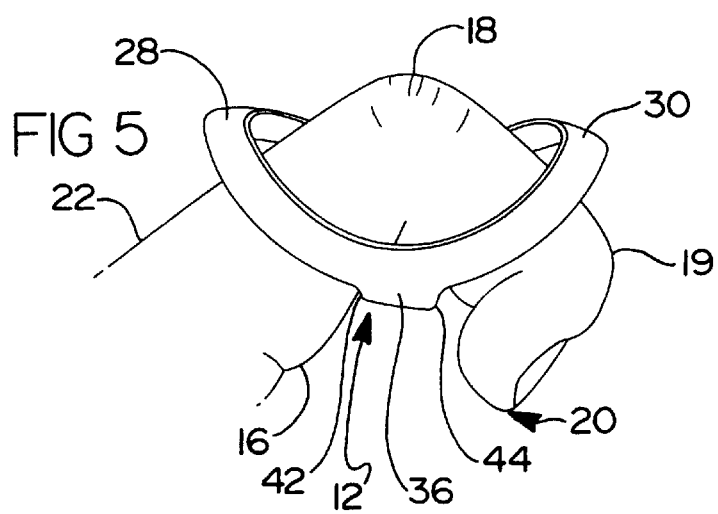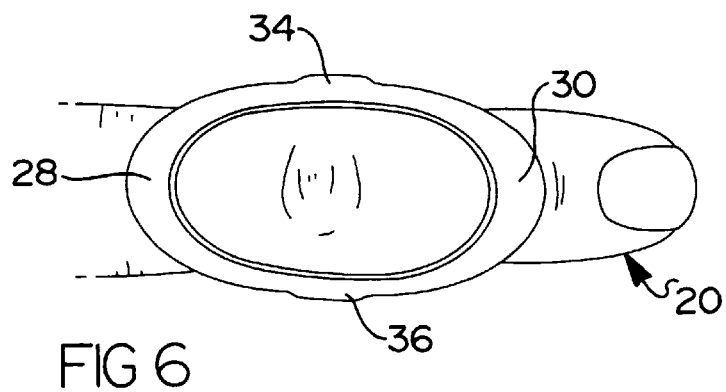

DIGIT SPLINT DEVICE AND METHOD OF USE

CROSS-REFERENCE TO RELATED APPLICATION

This application is a completion application of a co-pending U.S. Provisional Patent Application Serial No. 60/064,968 entitled "FINGER RING SPLINT DEVICE AND METHOD OF USE" filed Nov. 8, 1997, the disclosure of which is hereby incorporated by reference.

BACKGROUND OF THE INVENTION

1. Field of the Invention

The present invention relates to orthopedic splint type devices. Specifically, the invention relates to readily applicable and removable hyperextension limiting and stability enhancing restraining splints for the joints of digits.

2. Description of Prior Art

Several disease processes including Rheumatoid Arthritis (RA) and Osteoarthritis (OA) may adversely affect the mobility and stability of the joints of the body. Both these diseases, along with traumatic incidents that break or crush the fingers, will cause the internal forces acting upon the finger joints to become disrupted and will lead to deformities of the joints that restrict their motion or cause the joints to be unstable in one or more planes of motion. Specifically, the interphalangeal (IP) joints of the fingers of persons with arthritis will frequently become swollen and the bone structure affected in such a way that there is a loss of deliberate control of the tendons and muscles that act to move the joints through the full range of flexion and extension.

Joint instability at the proximal interphalangeal (PIP) joint and the distal interphalangeal (DIP) joint in the transverse plane results in loss of pinch prehension as the fingers deviate laterally towards the ulnar side of the hand and away from the force applied by the thumb in an attempt to achieve prehension for the performance of functional tasks. Joint instability in the sagittal plane of flexion and extension results in hyperextension, that is, extension past a neutral position of a finger, which disturbs the biomechanical forces from the tendons, ligaments and muscles that act upon the joint and results in a deformity known as the "swan-neck deformity". In this deformity, the PIP joint assumes a hyperextended position in a dorsal direction, away from the palm of the hand, and the DIP joint assumes a flexed posture, bending towards the palm, and results in a loss of extension to the neutral position.

This deformity may also persist following a traumatic injury to the finger joints that results in a fracture of one or more of the phalanges or that results in damage to the tendons, ligaments or muscles that control the finger. Most commonly, a fracture affecting the most distal phalanx, as very frequently occurs during participation in activities using a ball, and commonly known as a "baseball" or "mallet" finger, will result in a loss of extension away from the palm at the DIP joint and to instability of the joint in the sagittal plane. When uncorrected and unsupported, this deformity will often lead to a "swan-neck deformity" over time as the forces acting upon the fingers are altered in their alignment to the finger and eventually cause hyperextension and instability at the PIP joint which cannot be overcome by voluntary muscle control.

There are a variety of splints currently available to help support these unstable joints so as to impart stability to prohibit excessive and uncontrolled hyperextension or to restore range of motion to the finger joints. One variety of splints dynamically extends or flexes the joints through the forces supplied by elastic components, such as rubber bands, coiled metal springs, and spring metal wire, each having the characteristic of returning to its originally designed shape when forced into the opposite direction. The prior art splints of this variety have a drawback in that they have movable component parts and do not impart stability.

A second variety of splints, as disclosed in U.S. Pat. No. 4,270,528 issued to Hanson and U.S. Pat. Nos. 4,770,166 and 4,932,396 issued to Garris, is embodied by a ring-type structure. The ring-type structure of the Garris patent is generally made of precious metals such as gold and silver. The ring-type structure of the Hanson patent is generally made of metal such as stainless steel.

The second variety of splints, also, exhibits several drawbacks. Most importantly, these prior art splints do not provide lateral stability at the IP joints of the finger or generally correct flexion at the IP joints of the finger. Additionally, due to the narrow bands utilized to achieve the tubular ring-type design, the bands of the splints apply excessive pressure on the top of the finger, particularly in the presence of mallet finger deformities where the wearer must forcefully attempt to extend the PIP joint in order to achieve full extension at the DIP joint. Since these splints offer no adjustments in size, the bands of these splints may also constrict the finger, particularly if the finger is swollen. Another deficiency is that the splints require custom sizing and ordering through a health care professional thereby restricting access and, in many cases, being cost prohibitive. Finally, splints being embodied as metal rings may be undesirable for persons not wishing to draw attention to their deformities.

A third kind of splint is embodied in U.S. Pat. No. 3,170,460 ('460 patent) issued to Stilson. Stilson describes a splint for preventing hyperextension which constrains the finger through several points of supportive contact. The points of contact are through forward and rearward transversely disposed dorsal bridging braces and a cooperating palmar side joint seating saddle which are joined by linking components. The seating saddle is positioned beneath the center joint of the finger and the linking components are curved to maintain the geometrical relationship between the bridging braces and the seating saddle.

However, the third kind of splint, like the second variety of splints, exhibits several drawbacks. Most importantly, the splint of the '460 patent does not provide lateral stability at the IP joints of the finger or generally correct flexion at the IP joints of the finger. The splint is also deficient in that it offers no adjustments in size. As a result, the splint may either constrict the finger or migrate from the desired position on the finger.

It is therefore a goal of the present invention to overcome the problems heretofore encountered in the prior art. It is the purpose of the present invention to provide a splint that may be worn on a digit to: 1) limit hyperextension and provide lateral stability at the IP joints of a digit; or 2) correct flexion and provide lateral stability at the IP joints of a digit.

It is a further purpose of the present invention to provide a splint which contains an adjustment for size and does not require custom sizing and ordering through a health care professional. This will allow the splint to be more accessible and cost-effective than previously possible.

It is a still further purpose of the present invention to provide a splint made from materials which withstand repeated or aggressive activities so as to improve convenience and cost-effectiveness.

BRIEF SUMMARY OF THE INVENTION

In accordance with the present invention, there is provided, in a first aspect, a digit splint, generally, comprising:

(a) an arcuate angularly inclined base, the base having a first edge and a second edge and being positionable under a joint of a digit of a user; and (b) an ovoid formed integrally with the base and extending upwardly and radially outward therefrom and being positionable on the dorsum of a digit of a user, the ovoid being angularly inclined to conform to the dorsum of a digit of a user when a digit is in an extended position without hyperextension, the ovoid having a proximal portion, a distal portion, a medial side and a lateral side, the lateral side spaced apart from and substantially parallel to the medial side, the medial side and the lateral side cooperating to define two substantially parallel sides, the proximal portion being conformed to impinge upon the dorsum of a more proximal phalanx of a digit of a user and the distal portion being conformed to impinge upon the dorsum of a more distal phalanx of a digit of a user when a digit is in a fully extended position without hyperextension, and the two substantially parallel sides being conformed to impinge on the sides of the joint of a digit at the axis of the joint of a digit to provide lateral stability at the joint of a digit and to prevent migration of the splint on a digit and wherein the splint prevents hyperextension of the joint of a digit.

It is to be appreciated that the splint of the present invention can be used on any digit such as a finger, thumb or toe. Preferably, the splint is used on a finger. Any terminology herein with respect to the utilization of the splint is intended to encompass use on a finger, thumb or toe.

It is also to be appreciated that the splint of the present invention may be positioned on any desired joint of a digit such as the DIP or PIP joint.

The splint of the present invention overcomes disadvantages of the prior art by providing a splint having an ovoid formed integrally with a base and extending upwardly and radially outward therefrom. The ovoid is positionable on the dorsum of a finger of a user and is angularly inclined to conform to the dorsum of a finger of a user when a finger is in an extended position, without hyperextension. The ovoid distributes the pressure that occurs when there is forceful extension required to bring the finger into extension at the PIP or DIP joints and lessens the likelihood that the user will experience any discomfort from the splint.

The ovoid has two substantially parallel sides, the medial side and the lateral side, which impinge on the side of the PIP or DIP joints of a finger at the axis of the DIP or PIP joints. In cooperation with the base, the two substantially parallel sides resist migration of the splint on the finger both at rest and upon motion. The parallel sides also provide lateral stability at an IP joint, as the finger bends into flexion towards the palm.

The base of the splint, which is positionable on the palmar surface of a finger of a user at an IP joint of a finger, has a first edge and a second edge. The second edge is angularly inclined with respect to the first edge to provide a small alteration of fit for a user. The first edge and the second edge of the base are of a sufficient width to provide stability on the palmar surface of the PIP or DIP joint while still allowing for full bending of the joint towards the palm.

Alternatively, the splint may be oriented 180 degrees about the horizontal axis of a finger from that described above and worn on a joint of a finger, and is preferably, worn on the DIP joint of a finger. When the splint is worn on the DIP joint of a finger, the distal phalanx is maintained in extension while allowing flexion of the PIP joint. The fingertip of a finger also remains freely functional. In all other respects, the present invention remains the same.

The splint of the present invention is, preferably, manufactured from skin tone material which is aesthetically attractive and of low visibility so that a user may wear one or more of the splints without drawing attention to the user's hands or fingers.

The splint is presented in a range of sizes for the convenience of the user to choose the size which offers the greatest support and comfort.

In a second aspect, the present invention provides a method of manufacturing the splint hereof comprising:

(a) molding the splint as a continuous form without palpable seams from a lightweight, temperature-resistant, water-resistant material; and (b) sizing the splint to equal a standard jeweler's ring size.

The substantially seamless design affords greater strength than capable with finger splints manufactured with palpable seams. The materials used for the splint are light in weight and capable of withstanding temperature changes and exposure to water without changing size or temperature.

The present invention will be more clearly understood with reference to the accompanying drawings, in which like reference numerals refer to like parts.

BRIEF DESCRIPTION OF THE SEVERAL VIEWS OF THE DRAWING

FIG. 4 is a side view of a finger splint according to the present invention in position on an extended finger;

FIG. 5 is a side view of a finger splint hereof in position on the flexed finger hereof;

FIG. 6 is a top down view of a finger splint according to the present invention in position on an extended finger;

DETAILED DESCRIPTION OF THE INVENTION

Figure 1:
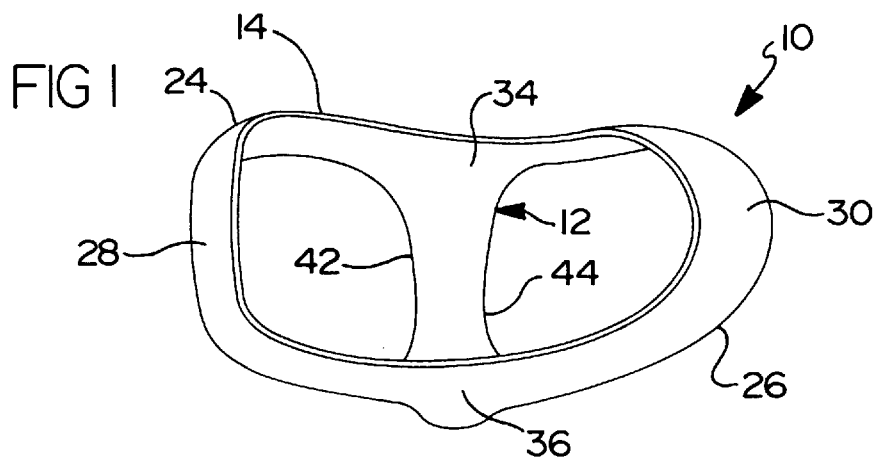
FIG. 1 is a perspective top plan view of a finger splint according to the present invention.

At the outset, it is to be noted that the present splint is intended to be used with a "digit" which for purposes of the present invention is defined as a finger, thumb, or toe and, preferably, a finger. Each digit includes a joint which serves as a point of connection between a more proximal phalanx and a more distal phalanx. The terms "proximal" and "distal" are known to one of ordinary skill in the medical art. A joint as defined in the present invention includes an IP joint.

For purposes of illustration, the present invention will be generally described with reference to a finger. A finger, generally, includes a metacarpophalangeal (MP) joint, a proximal phalanx, a proximal interphalangeal (PIP) joint, a middle phalanx, a distal interphalangeal (DIP) joint and a distal phalanx.

For purposes of illustrating the present invention, an interphalangeal (IP) joint refers to either the PIP joint or the DIP joint. The IP joints of the digits are single axis hinged joints with a single degree of freedom in flexion and extension. The thumb contains one distal IP joint and the four fingers each have a PIP joint and a DIP joint. The PIP is comprised of a distal end of a proximal phalanx articulating with a proximal head of a middle phalanx. The DIP is comprised of a distal end of a middle phalanx articulating with a proximal end of a distal phalanx.

The present invention provides in a first aspect, a digit splint, generally, comprising:

(a) an arcuate angularly inclined base, the base having a first edge and a second edge and being positionable under a joint of a digit of a user; and (b) an ovoid formed integrally with the base and extending upwardly and radially outward therefrom and being positionable on the dorsum of a digit of a user, the ovoid being angularly inclined to conform to the dorsum of a digit of a user when a digit is in an extended position without hyperextension, the ovoid having a proximal portion, a distal portion, a medial side and a lateral side, the lateral side spaced apart from and substantially parallel to the medial side, the medial side and the lateral side cooperating to define two substantially parallel sides, the proximal portion being conformed to impinge upon the dorsum of a more proximal phalanx of a digit of a user and the distal portion being conformed to impinge upon the dorsum of a more distal phalanx of a digit of a user when a digit is in a fully extended position without hyperextension, and the two substantially parallel sides being conformed to impinge on the sides of the joint of a digit at the axis of the joint of a digit to provide lateral stability at the joint of a digit and to prevent migration of the splint on a digit and wherein the splint prevents hyperextension of the joint of a digit.

With more particularity and with reference now to FIGS. 1–6, there is shown therein, a digit splint 10 in accordance herewith. The splint 10 inhibits hyperextension of an interphalangeal joint of a finger of a user, provides lateral stability at an interphalangeal joint as a finger of a user bends into flexion towards the palm of a hand, and prevents migration of the splint 10 on a finger of a user. As defined herein, the splint 10 comprises an arcuate angularly inclined base 12 and an ovoid 14 formed integrally therewith and extending upwardly and radially outwardly therefrom. The base 12 is positionable on the palmar surface 16 of an interphalangeal joint 18 and 19 of a finger 20 of a user. Likewise, the ovoid 14 is positionable on the dorsum 22 of a finger 20 of a user. The ovoid 14 is angularly inclined to conform to the dorsum 22 of a finger 20 of a user when a finger 20 is in an extended position without hyperextension.

Figure 2:
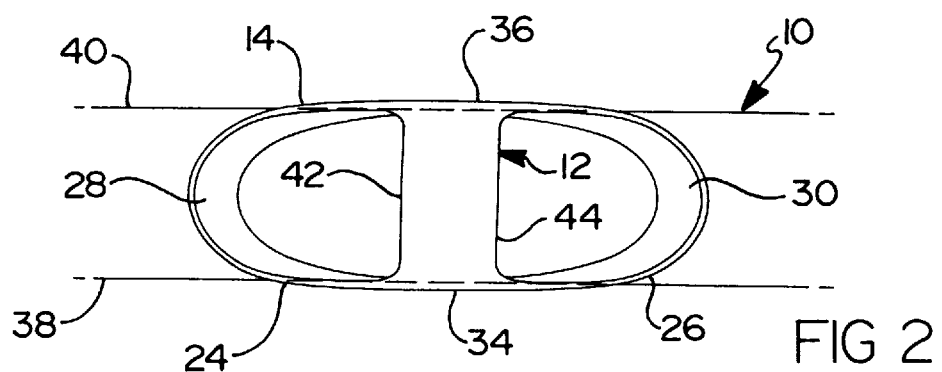
FIG. 2 is a bottom view of a finger splint according to the present invention.

As best seen in FIGS. 1, 2 and 6, the ovoid 14 has a pair of opposed substantially "U" shaped portions, defined herein as the proximal portion 24 and the distal portion 26. Each of the pair of opposed substantially "U" shaped portions has a bight section 28 and 30 respectively. The ovoid 14 is angularly inclined to conform to the dorsum 22 of a finger.

The proximal bight section 28 of the ovoid 14 and the distal bight section 30 of the ovoid 14 lie substantially in a first plane 32 (FIG. 3) which is substantially horizontal to a line drawn longitudinally along a finger 20 and which bisects the PIP joint 18 of the finger 20 of a user when the finger 20 is in the fully extended position. Stated alternatively, the first plane 32 is substantially horizontal to the mid-longitudinal axis of a finger 20.

The medial side 34 of the ovoid 14 lies in a second plane 38 parallel to the mid-longitudinal axis of a finger 20 when the finger 20 is in a fully extended position. Likewise, the lateral side 36 of the ovoid 14 lies in a third plane 40 parallel to the mid-longitudinal axis of a finger 20 when the finger 20 is in a fully extended position.

As shown, the angular inclination of the ovoid 14 is such that the second plane 38 and the third plane 40 are substantially perpendicular to the first plane 32.

The medial side 34 and the lateral side 36, which cooperate to define two substantially parallel sides, are spaced apart from and are substantially parallel to each other. The medial side 34 impinges on or is in continuous contact with the medial side of an interphalangeal joint 18 or 19 of a finger 20 at the axis of the IP joint 18 or 19 and the lateral side 36 impinges on or is in continuous contact with the lateral side of an interphalangeal joint 18 or 19 at the axis of the IP joint 18 or 19 of a finger 20. Thus, the two substantially parallel sides 34 and 36 impinge on the sides of an interphalangeal joint 18 or 19 of a finger 20 at the axis of the IP joint 18 or 19. The positioning of the parallel sides 34 and 36 at the axis of the IP joint 18 or 19 provides lateral stability to a finger 20 at an interphalangeal joint 18 or 19 of a finger 20 and prevents migration of the splint 10 on a finger 20 of a user whether at rest or in motion.

As shown in FIG. 6, the ovoid 14 conforms to the dorsum 22 of a finger 20 and the parallel sides 34 and 36 impinge at the axis of the joint of a finger such that the splint 10 provides lateral stability to a finger 20 at the interphalangeal joint 18 or 19 of the finger 20 and prevents migration of the splint 10 on a finger 20. The ovoid 14 is in continuous contact with a finger 20 when the finger 20 is in a fully extended position.

Figure 3:
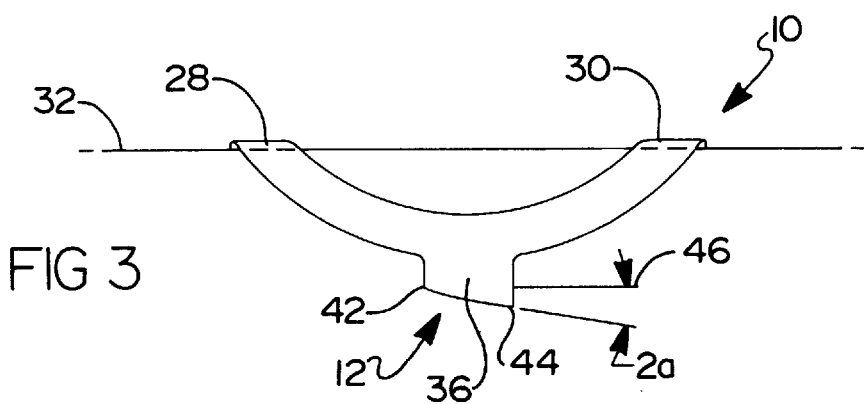
FIG. 3 is a side view of a finger splint hereof.

As seen in FIGS. 3 and 5, the base 12 which, in use, is positioned on the palmar surface 16 of an interphalangeal joint 18 and 19 has a first edge 42 and a second edge 44. The first edge 42 of the base 12 lies in a fourth plane 46 which is parallel to the mid-longitudinal axis of a finger 20 when the finger 20 is in a fully extended position without hyperextension. The second edge 44 of the base 12 is angularly inclined at an angle 2a up to about 10 degrees with respect to the fourth plane 46. The angle 2a enables a small alteration of fit when the ovoid 14 is positioned such that the proximal portion 24 impinges upon the dorsum 22 of the more proximal phalanx of a finger 20 and the distal portion 26 impinges upon the dorsum 22 of the more distal phalanx of a finger 20. Furthermore, in the event, and as discussed below, of a fluctuation in size of a finger 20 of a user, the small alteration of fit enables the splint 10 to be turned 180 degrees such that the distal portion 26 may be positioned on the more proximal phalanx of a finger 20 of a user and the proximal portion 24 may be positioned on the more distal phalanx.

The base 12 has a width sufficient to provide stability on the palmar surface 16 of the interphalangeal joint 18 and 19 while allowing full flexion or bending of the PIP joint 18 or DIP joint 19 around the base 12 towards the palmar surface 16 of the hand of a user.

In FIG. 4, there is shown the splint 10 restraining the final degrees of extension of the PIP joint 18 of a finger 20. The ovoid 14 distributes the pressure that occurs when there is a forceful extension bringing the finger 20 into extension at the PIP joint 18 or the DIP joint 19 and lessens the likelihood that a user will experience any discomfort from the splint 10.

Figure 7:
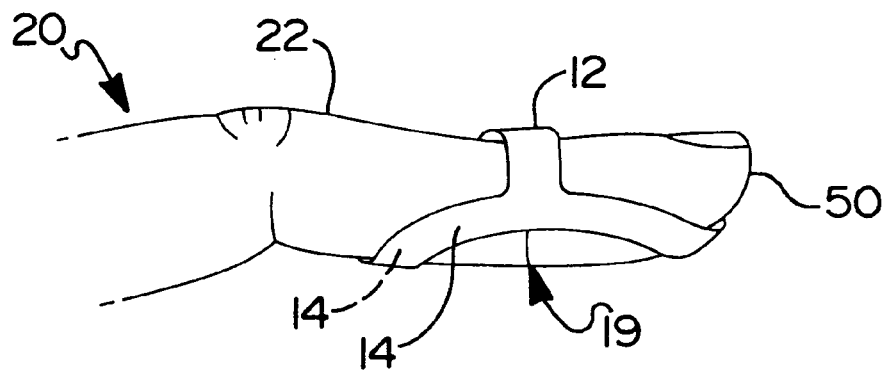
FIG. 7 is a side view of a second positioning of a finger splint according to the present invention in position on an extended finger.
Figure 8:
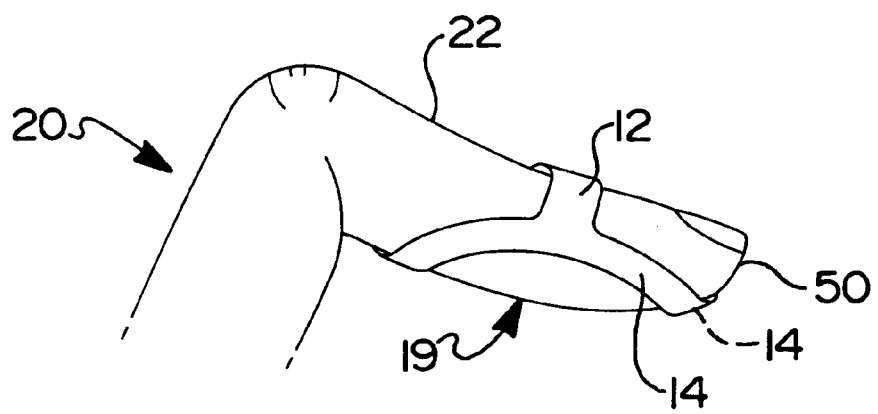
FIG. 8 is a side view of the second positioning of a finger splint hereof in position on a flexed finger.

Alternatively, as shown in FIGS. 7 and 8, the splint 10 may be oriented 180 degrees about the horizontal axis from that shown in FIGS. 1–6 and worn on a joint of a finger.

Preferably, the splint is worn on the DIP joint 19 of a finger 20. In this configuration, the base 12 impinges on the dorsum 22 of the DIP joint 19 of a finger 20 and the ovoid 14 impinges on the palmar surface 16 of a finger 20 to maintain the distal phalanx in extension while allowing flexion of the PIP joint 18. The fingertip 50 of a finger 20 also remains freely functional.

The configuration of the splint shown in FIGS. 7–8 provides lateral stability at a joint of a digit and corrects flexion at a joint of a digit. In all other respects, the present invention remains the same as the embodiment described with respect to FIGS. 1–6.

The splint 10 is hereby, preferably, manufactured from a light-weight, temperature-resistant, water-resistant material such as semi-flexible plastic or resin of sufficient rigidity. A suitable material includes, but is not limited to, polypropylene and polyethylene. Such material resists deformation as a finger 20 moves into extension yet can be slightly deflected at the base 12 to increase the angle 2a in order to facilitate placement and removal of the splint 10 upon a finger 20 of a user.

The material may be pigmented to provide a skin tone color. The skin tone color of the material is aesthetically attractive and of low visibility so that a user may wear one or more of the splints of the present invention without drawing attention to the hands or fingers of the user.

Thus, in a second aspect, the present invention provides for a method of manufacturing the splint 10. The method, generally, comprises: (a) molding the splint as a continuous form without palpable seams; (b) casting the splint from a light-weight, temperature-resistant, water-resistant material; and (c) sizing the splint to equal a standard jeweler's ring size. Preferably the splint is molded utilizing an injection molding process in a multi-cavity mold. The mold is preferably made of metal such as stainless steel or aluminum.

By choosing the suitable material as disclosed hereinabove, the splint 10 is comfortable for a user to wear in all weather conditions. In molding the splint 10, the radius of the base 12 is selected and sized to equal a jeweler's standard ring size. The jeweler's standard ring size is a size which is well known to one of ordinary skill in the jewelry industry. The standard ring size may be a full standard ring size or a half standard ring size.

The splint 10 is preferably cast in at least 8 sizes which correspond to the jeweler's standard ring size. The range of sizes is provided for the convenience of a user so that the user may choose the standard ring size which offers the greatest support and comfort. The present invention provides an advantage in that the splint 10 does not require custom sizing and ordering through a health care professional thereby restricting access of the splint to a user and in many cases being cost prohibitive. As disclosed hereinabove, the small alteration of fit provided by the angle 2a corresponds to one half of a standard ring size thereby allowing the splint 10 to be fit on a finger 20 of a user which corresponds to a full standard ring size or a half standard ring size.

Molding the splint 10 as a continuous form without palpable seams from the lightweight, temperature-resistant, water-resistant material provides a durable light-weight splint which is minimally invasive. The substantially seamless design affords greater strength to the splint 10 than previous designs with seams.

It is also to be appreciated that the user of the present invention may wear as many splints as necessary and desired, to inhibit hyperextension and provide lateral stability to the affected digits such as fingers, thumbs or toes.

Although the present invention has been described herein with respect to a specific embodiment thereof, it will be understood that the foregoing description is intended to be illustrative, and not restrictive. Many modifications of the present invention will occur to those skilled in the art to which the present invention is directed.

Having thus described the invention, what is claimed is:

1. A digit splint comprising:
   (a) an arcuate, angularly inclined base, the base having a first edge and a second edge and being positionable under a joint of a digit of a user, wherein the first edge of the base lies in a plane, and further wherein the second edge of the base inclines from the plane at an acute angle greater than zero degrees, the plane being substantially parallel to a mid-longitudinal axis of a digit of a user when a digit is in a fully extended position without hyperextension; and
   (b) an ovoid formed integrally with the base and extending upwardly and radially outward therefrom and being positionable on the dorsum of a digit of a user, the ovoid being angularly inclined to conform to the dorsum of a digit of a user when a digit is in an extended position without flexion, the ovoid having a proximal portion, a distal portion, a medial side and a lateral side, the lateral side spaced apart from and substantially parallel to the medial side, the medial side and the lateral side cooperating to define two substantially parallel sides, the proximal portion being conformed to impinge upon the dorsum of a more proximal phalanx of a digit of a user and the distal portion being conformed to impinge upon the dorsum of a more distal phalanx of a digit of a user when a digit is in a fully extended position without flexion, and-the two substantially parallel sides being conformed to impinge on the sides of the joint of a digit at the axis of the joint of a digit to provide lateral and medial stability at the joint of a digit and to prevent migration of the splint on a digit and wherein the splint prevents hyperextension and deviation of the joint of a digit.

2. The splint of claim 1, wherein the first edge of the base lies in a plane, and further wherein the second edge of the base is angularly inclined from an angle greater than zero degrees to about ten degrees with respect to the plane, the plane being horizontal to a mid-longitudinal axis of a digit of a user when a digit is in a fully extended position without hyperextension.

\* \* \* \* \*